US008146446B1

(12) United States Patent
Wick

(10) Patent No.: US 8,146,446 B1
(45) Date of Patent: Apr. 3, 2012

(54) CONCENTRATOR DEVICE AND METHOD OF CONCENTRATING A LIQUID SAMPLE

(75) Inventor: Charles H. Wick, Darlington, MD (US)

(73) Assignee: The United States of America, as represented by the Secretary of the Army, Washington, DC (US)

( * ) Notice: Subject to any disclaimer, the term of this patent is extended or adjusted under 35 U.S.C. 154(b) by 539 days.

(21) Appl. No.: 12/401,013

(22) Filed: Mar. 10, 2009

(51) Int. Cl.
*G01N 1/18* (2006.01)

(52) U.S. Cl. .................................... 73/863.23

(58) Field of Classification Search ............... 73/863.23
See application file for complete search history.

(56) References Cited

U.S. PATENT DOCUMENTS

| | | | | | |
|---|---|---|---|---|---|
| 1,905,806 | A | * | 4/1933 | Clark | 210/327 |
| 2,987,472 | A | * | 6/1961 | Kollsman | 210/652 |
| 5,400,665 | A | * | 3/1995 | Zhu et al. | 73/863.12 |
| 5,614,154 | A | * | 3/1997 | Glatz et al. | 422/544 |
| 6,051,189 | A | * | 4/2000 | Wick et al. | 422/82.01 |
| 6,656,361 | B1 | * | 12/2003 | Herron et al. | 210/640 |
| 6,905,594 | B2 | * | 6/2005 | Ferguson | 210/90 |
| 7,018,533 | B2 | * | 3/2006 | Johnson et al. | 210/321.69 |
| 7,219,805 | B2 | * | 5/2007 | DeMaison | 209/246 |
| 7,435,339 | B2 | * | 10/2008 | Olivier et al. | 210/86 |
| 2008/0053828 | A1 | * | 3/2008 | Daniel et al. | 204/547 |
| 2008/0311672 | A1 | * | 12/2008 | Dasgupta et al. | 436/161 |
| 2010/0260815 | A1 | * | 10/2010 | Kyle et al. | 424/422 |

* cited by examiner

*Primary Examiner* — Hezron E Williams
*Assistant Examiner* — Mark A Shabman
(74) *Attorney, Agent, or Firm* — Ulysses John Biffoni

(57) ABSTRACT

A concentrator device and method of concentrating a liquid sample may be provided. The concentrator device may include a pressure vessel and a filter element disposed within the pressure vessel. The pressure vessel may include an inlet configured to introduce pressurized air into a first portion of the pressure vessel and a first outlet fluidly coupled with a second portion of the pressure vessel. The first outlet may be adapted to be selectively opened and closed. A second outlet may be configured to receive a capillary tube inserted into the first portion of the pressure vessel. The filter element may be configured to receive a liquid sample to be concentrated. The filter element may substantially separate the first portion of the pressure vessel from the second portion of the pressure vessel and may define a retentate side adjacent to the first portion and a filtrate side adjacent to the second portion. When pressurized air is introduced through the inlet and the first outlet is open, a filtrate of the liquid sample received in the filter element may pass from the retentate side to the filtrate side such that a concentrated retentate of the liquid sample remains on the retentate side. When the first outlet is closed, the concentrated retentate of the liquid sample may be forced out through the capillary tube.

11 Claims, 6 Drawing Sheets

CONCENTRATOR DEVICE AND METHOD OF CONCENTRATING A LIQUID SAMPLE

GOVERNMENTAL INTEREST

The invention described herein may be manufactured, used and licensed by or for the U.S. Government.

BACKGROUND

1. Field of Invention

The invention may relate to devices, systems, and/or methods for concentrating a liquid sample and to the detection, identification, and monitoring of submicron-sized particles in the concentrated sample such as, for example, viruses, virus-like agents, prions, viral subunits, viral cores of dilapidated viruses, etc.

2. Related Art

Detection and identification of viruses pathogenic to humans in an environment without limiting the detection and identification to a particular family, genus and species can be difficult, particularly in combat conditions such as, for example, a potential biological warfare (BW) threat environment. Instruments are needed which enable detection of, for example, remote releases of biological agents in a field environment, thereby providing early warning capabilities and allowing calculations for troop movements and wind patterns.

In the detection and monitoring of viruses, false positives associated with background materials can be a major obstacle. Background materials may include biological or other debris which obscures the detection of the viruses by registering as a virus when a sample is analyzed. Analysis of viruses requires a high degree of purification of those viruses to overcome background loading in order to avoid false positives. For example, a BW virus may be buried within loadings of other microorganisms which form biological debris having loading on a magnitude of $10^{10}$ larger than the threshold loading for the targeted virus itself.

Methods that culture viruses can often be used to increase the virus over background material. Culture methods, however, may be too slow for effective viral BW detection. Furthermore, some important viruses cannot be easily cultured.

Viruses may also be extracted from an environment and concentrated to an extent that permits detection and monitoring of viruses, without culturing procedures. Generally, in the detection of small amounts of viruses in environmental or biological liquids, it is necessary to both enrich the concentration of viruses many orders of magnitude (i.e., greatly reduce the volume of liquid solubilizing the viruses) and accomplish removal of non-viral impurities. In the presence of non-viral impurities, even the most sensitive detection methods generally require virus concentrations on the order of 10 femtomoles/microliter or more in the sampled liquid to reliably detect the viruses. In general, a standard method for the concentration of virus samples involves a tangential flow (cross-flow) filtration system to reduce the volume of the sample while removing impurities such as salts and small cellular debris. A more practical and effective device is needed, for example, for use with a capillary inlet of a gas-phase electrophoretic mobility molecular analysis (GEMMA) device.

SUMMARY

In an embodiment of the invention, a liquid sample concentrator device may include a pressure vessel and a filter element disposed within the pressure vessel. The pressure vessel may include an inlet configured to introduce pressurized air into a first portion of the pressure vessel and a first outlet fluidly coupled with a second portion of the pressure vessel. The first outlet may be adapted to be selectively opened and closed. A second outlet may be configured to receive a capillary tube inserted into the first portion of the pressure vessel. The filter element may be configured to receive a liquid sample to be concentrated. The filter element may substantially separate the first portion of the pressure vessel from the second portion of the pressure vessel and may define a retentate side adjacent to the first portion and a filtrate side adjacent to the second portion. When pressurized air is introduced through the inlet and the first outlet is open, a filtrate of the liquid sample received in the filter element may pass from the retentate side to the filtrate side such that a concentrated retentate of the liquid sample remains on the retentate side. When the first outlet is closed, the concentrated retentate of the liquid sample may be forced out through the capillary tube.

In an embodiment of the invention, a method for concentrating a liquid sample may be provided. The method may include introducing a predetermined amount of a liquid sample to be concentrated into a filter element disposed within a pressure vessel. The method may include introducing pressurized air into a first portion of a pressure vessel on a retentate side of the filter element. The method may include opening a first outlet fluidly coupled with a second portion of the pressure vessel, whereby a filtrate of the liquid sample passes through the filter element to the second portion from the retentate side. The method may include closing the first outlet when a predetermined amount of the liquid sample remains on the retentate side of the filter or after a predetermined amount of time, whereby when the first outlet is closed, a concentrated retentate of the liquid sample is forced through an inlet end of a capillary tube positioned proximate the retentate side of the filter element.

This summary is provided merely to introduce certain concepts and not to identify any key or essential features of the claimed subject matter. Further features and advantages, as well as structure and operation of an embodiment of the invention, are described in detail below with reference to the accompanying drawings.

BRIEF DESCRIPTION OF THE DRAWINGS

The foregoing and other features and advantages of the invention will be apparent from the following, more particular description of an embodiment of the invention, as illustrated in the accompanying drawings wherein like reference numbers generally indicate identical, functionally similar, and/or structurally similar elements. Unless otherwise indicated, the accompanying drawing figures are not to scale.

DETAILED DESCRIPTION

Figure 1:
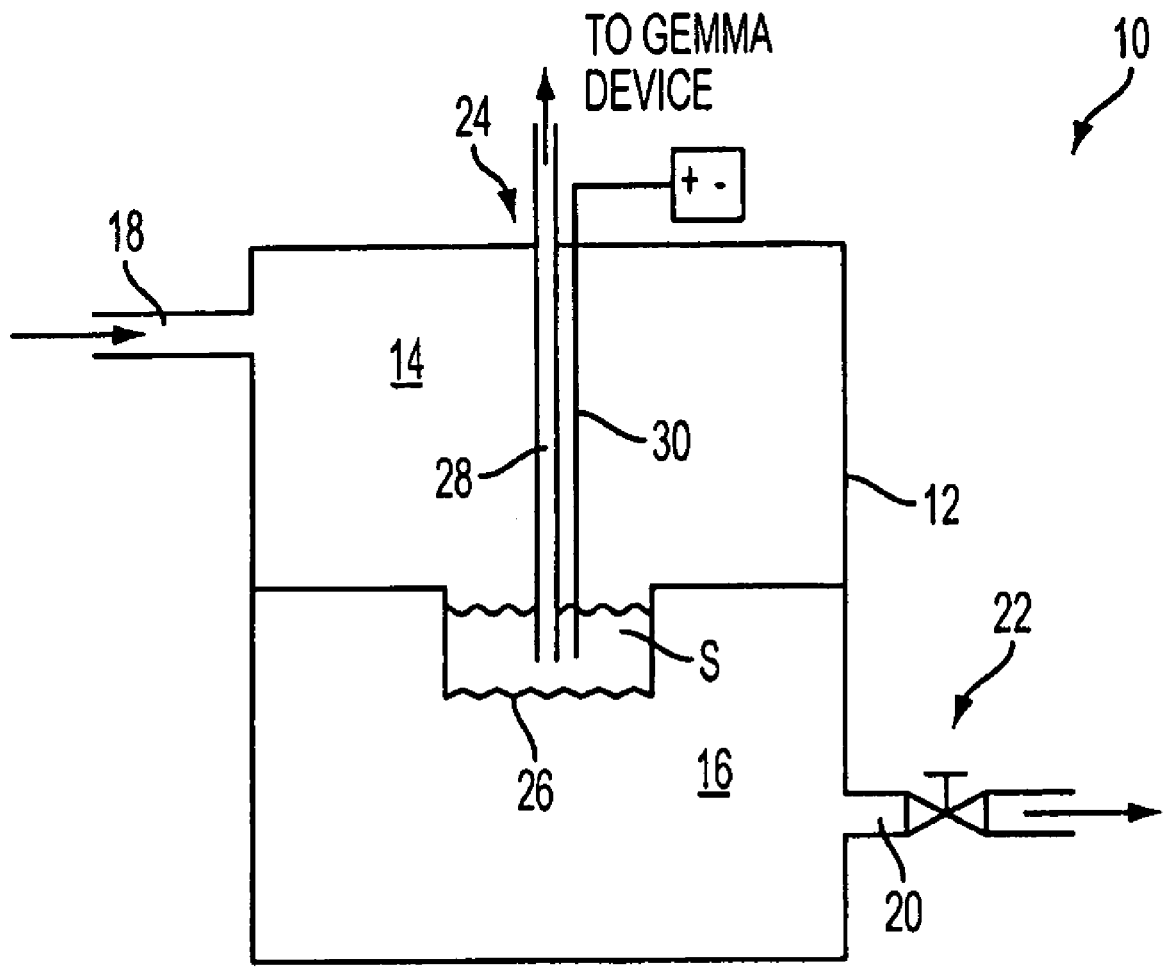
FIG. 1 depicts a schematic and illustrative view of a concentrator device to concentrate a liquid sample according to an embodiment of the invention.

An embodiment(s) of the invention is discussed in detail below. While an embodiment is discussed, specific terminology is employed for the sake of clarity. However, the invention is not intended to be limited to the specific terminology so selected and it should be understood that this is done for illustration purposes only. A person skilled in the relevant art will recognize that other components and configurations can be used without parting from the spirit and scope of the invention defined by the claims. Each specific element includes all technical equivalents that operate in a similar manner to accomplish a similar purpose.

In the following description of an embodiment of the invention, directional words such as, for example, "top," "bottom," "left," "right," "upwardly," and "downwardly," "clockwise," "counter-clockwise," are employed by way of description and not limitation with respect to the orientation of the device and its various components as illustrated in the drawings.

FIG. 1 depicts a schematic and illustrative view of a concentrator device (module) 10 constructed to concentrate a liquid sample S according to an embodiment of the invention. Filtered concentration of a liquid sample (e.g., volume reduction coupled with retention of specific submicron-sized particles), may allow for more effective detection, identification, and monitoring of submicron-sized particles in the sample S. As schematically shown in FIG. 1, the concentrator device 10 may include, for example, a pressure vessel 12 having a first portion 14 and a second portion 16. An inlet 18 may be configured to introduce pressurized air into the first portion 14 of the pressure vessel 12. A first outlet 20 may be fluidly coupled with the second portion 16 of the pressure vessel 12 and may be adapted to be selectively opened and closed with, for example, a valve mechanism 22. A second outlet 24 may be configured to receive a capillary tube 28 inserted into the first portion 14 of the pressure vessel 12. The capillary tube 28 may be coupled to an electrospray unit of a gas-phase electrophoretic mobility molecular analysis (GEMMA) device (not shown) as described, for example, in the "detection stage 104" in commonly owned U.S. Pat. Nos. 6,051,189, 6,485,686, 6,491,872, and 7,250,138, each of which is hereby incorporated by reference in its entirety.

A filter element 26 may be disposed within the pressure vessel 12 and may be configured to receive a liquid sample S to be concentrated. The filter element 26 may substantially separate the first and second portions 14, 16 of the pressure vessel 12. The filter element 26 may define a retentate side adjacent to the first portion 14 and a filtrate side adjacent to the second portion 16. An electrically conductive wire 30 such as, for example, a platinum wire, may be coupled to a voltage source of the electrospray unit of the GEMMA device (not shown) and may extend through the first portion 14 into the retentate side of the filter element 26 in order to establish a current return for the electrospray operation.

The liquid sample S may have an initial volume of, for example, approximately 500 μl when received in the filter element 26 within the pressure vessel 12. When pressurized air is introduced through the inlet 18 and the valve mechanism 22 at the first outlet 20 is open, a filtrate of the liquid sample S may pass from the retentate side to the filtrate side of the filter element 26 such that a concentrated retentate of the liquid sample S remains on the retentate side. The pressurized air may be, for example but not limited to, clean, regulated air supplied under approximately 3-4 psi, although other pressures may be sufficient depending upon the properties of the various components employed in the device, particularly the filter element 26. Once the concentrated retentate remaining on the retentate side of the filter element 26 reaches a predetermined volume such as, for example, approximately 80-100 μl, or alternatively, after a predetermined amount of time, the valve mechanism 22 of the first outlet 20 may be closed (e.g., manually by a user or automatically by a control device (not shown)). When the valve mechanism 22 of the first outlet 20 is closed, the remaining concentrated retentate of the liquid sample S may be forced out through the capillary tube 28 on to the electrospray unit of the GEMMA device (not shown).

In this way, the concentrator device 10 may utilize an existing overpressure at the capillary inlet of the electrospray unit to filter and concentrate a virus sample and thereby allow analysis with the GEMMA device without removal of the concentrated sample from an Integrated Virus Detection System (IVDS).

FIG. 2 depicts an exploded view of a concentrator device 100 according to an embodiment of the invention. The concentrator device 100 may include a pressure vessel 102 (see FIG. 3) having a hollow outer housing 104 and an inner (base) member 106 constructed to be removeably received in an open end of the hollow outer housing 104. The pressure vessel 102, including the housing 104 and the inner member 106, may be formed from any suitable material such as, for example, but not limited to, a thermoplastic material (e.g., poly(methyl methacrylate) (PMMA)), glass, metal, or a combination thereof. The concentrator device 100 may also include a filter element 108 constructed to receive a liquid sample to be concentrated and which may be received in the pressure vessel 102.

The hollow outer housing 104 may be, for example, a substantially cylindrical container, although other configurations and shapes are envisioned. The housing may have an open end and an inner surface 114 defining an interior volume. The housing 104 may include an inlet 112, a first outlet 122, and a second outlet 116. A valve mechanism 124, 126 may be coupled to the first outlet 122 and may be any suitable pressure release device including, for example, a thumb valve or the like. The valve mechanism may include an outlet 124 and a flow-control element 126 which may be adjustable between open and closed positions and may be manually operable or automatically controllable with a control device (not shown). The second outlet 116 may be configured to receive a threaded fitting 118 for receipt of a capillary tube from an electrospray unit of a GEMMA device (not shown in FIG. 2). An electrically conductive wire 120 may extend from the fitting 118 into the interior volume of the housing 104.

The inner member 106 may include a base portion and an upper portion 130 configured to be received through the open end of the hollow outer housing 104. Like the housing 104, the inner member 106 may be substantially cylindrical, although other configurations and shapes are envisioned. The upper portion 130 of the inner member 106 may include an outer surface 132 and may define an interior cavity 136 constructed to receive the filter element 108 when the concentrator device 100 is assembled. A passageway 138 between the interior cavity and the outer surface 132 may be provided. The upper portion 130 of the inner member 106 may also include one or more seal elements 140, 142 such as, for example, polymeric or rubber O-rings, disposed about the outer surface 132 at positions both above and below the passageway 138. When the concentrator device 100 is assembled and the inner member 106 is received in the housing 104, the interior cavity 136, passageway 138, may be fluidly coupled with the first outlet 122 by way of an annular volume defined (radially) between the outer surface 132 and inner surface 114 as well as (longitudinally) between seal elements 140, 142.

When assembled (see FIG. 3), the inner member 106 and the hollow outer housing 104 may be removeably coupled to one another by at least one of a friction fit, a snap fit, a bayonet connection, a fastener connection, a latch connection, and/or a threaded connection. In the embodiment depicted in FIGS. 2-3, a bayonet connection is shown wherein one or more pegs 144 may be disposed on the inner surface 114 of the housing 104 for receipt in one or more angled slots 146 defined on the outer surface 132 of the upper portion 130.

The filter element 108 may be a centrifugal ultrafiltration wedge filter such as, for example but not limited to, a Ultrafree®-0.5 Centrifugal Filter Unit, available from Millipore Corp. of Billerica, Mass., USA, having a predetermined molecular weight cut-off value (MWCO) of, for example but not limited to, 100K Da. The filter element 108 may include a filter membrane of, for example, polyethersulfone, and may define a retentate side 150 and a filtrate side 152. The filter element 108 may optionally be received in a filtrate receiver 110 having an opening 154 configured to allow fluid (or pressure) communication between the filtrate side 152 of the filter element 108 and the interior cavity 136 of the inner member 106.

Figure 2:
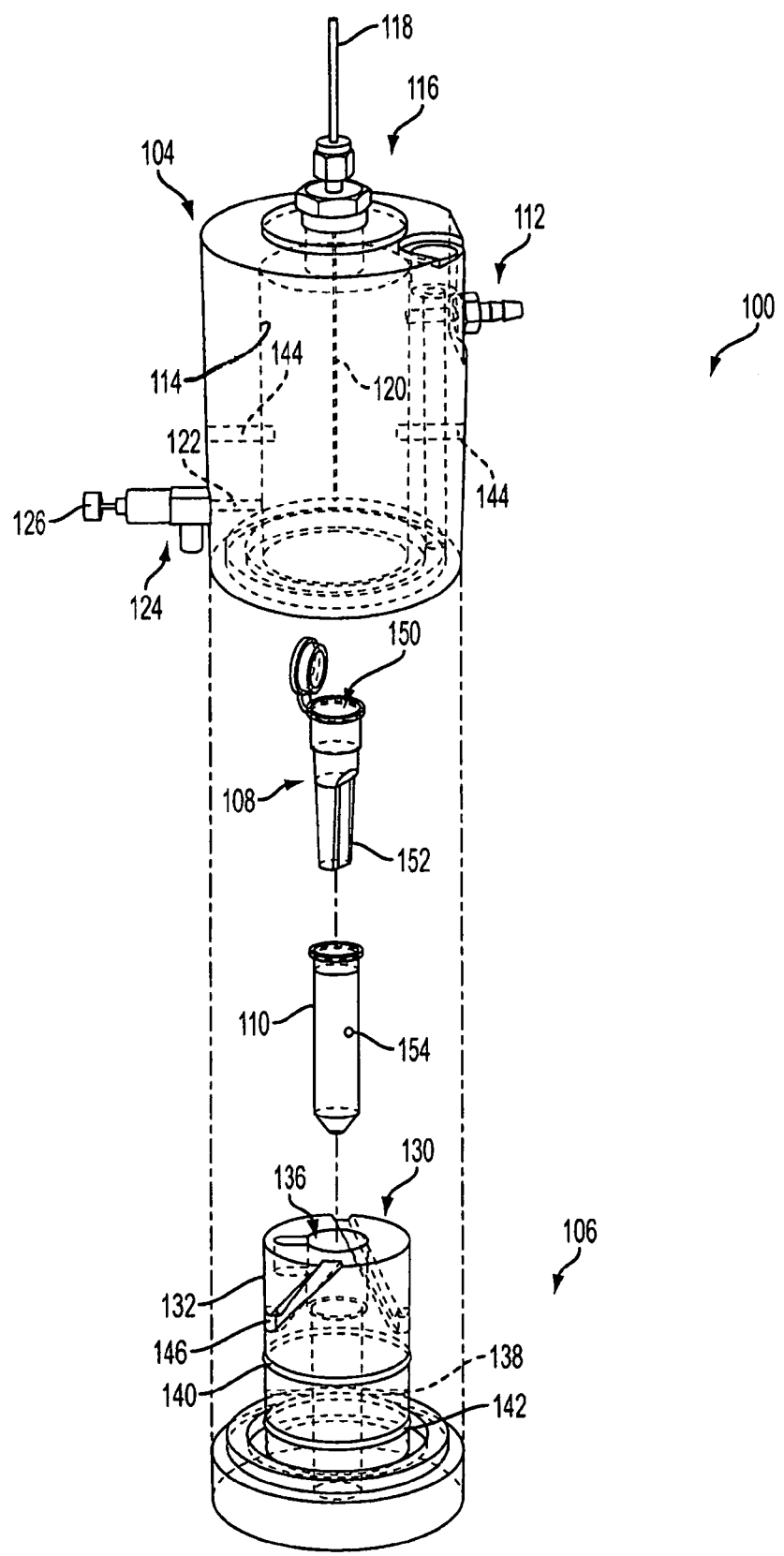
FIG. 2 depicts an exploded view of a concentrator device according to an embodiment of the invention.
Figure 3:
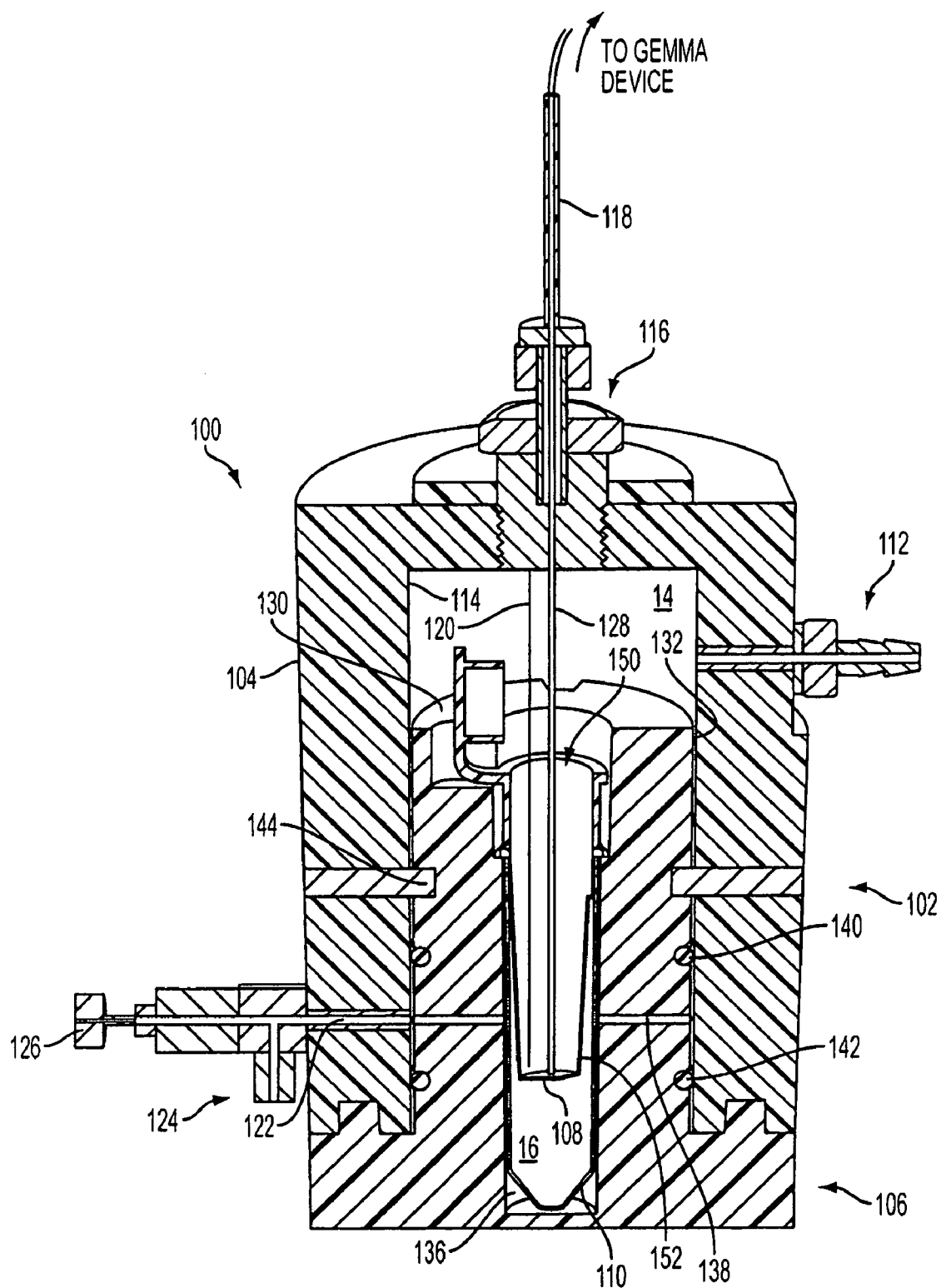
FIG. 3 depicts a cross-sectional view of the assembled concentrator device shown in FIG. 2.

FIG. 3 depicts a cross-sectional view of the assembled concentrator device 100 shown in FIG. 2. As shown in FIG. 3, the inner member 106 may be removeably received in the hollow outer housing 104 to define the pressure vessel 102. The filter element 108, containing a liquid sample S to be concentrated, may be received in the interior cavity 136 of the inner member 106. The pressure vessel 102 may be coupled to the electrospray unit of the GEMMA device (not shown) and a capillary tube 128 from the electrospray unit may extend through the fitting 118 at the second outlet 116 and into the liquid sample on, the retentate side 150 of the filter element 108. The electrically conductive wire 120 may also extend into the liquid sample on the retentate side 150 of the filter element 108 to establish a current return for the electrospray operation. Pressurized air (e.g., clean, regulated) at, for example, approximately 3-4 psi may be introduced through the inlet 112. The first outlet 122 may be opened by opening the valve mechanism 124, 126. A filtrate of the liquid sample S disposed in the filter element 108 may pass from the retentate side 150 to the filtrate side 152 so that a concentrated retentate of the liquid sample S remains on the retentate side 150. When a predetermined amount of the liquid sample S remains on the retentate side 150 of the filter element 150, or after a predetermined amount of time, the first outlet may be closed by closing the valve mechanism 124, 126, and the concentrated retentate of the liquid sample S may be forced out through the capillary tube 128.

The concentrator device 100 may be utilized as a modular handheld device or may be incorporated into an IVDS system. The device may eliminate a time consuming centrifugation step that can take upwards of 60 minutes. The concentrator device 100 may allow direct analysis of the liquid sample after concentrating. Tests were performed to determine concentration efficiency with a virus sample as shown in the following examples:

Example 1

Figure 4:
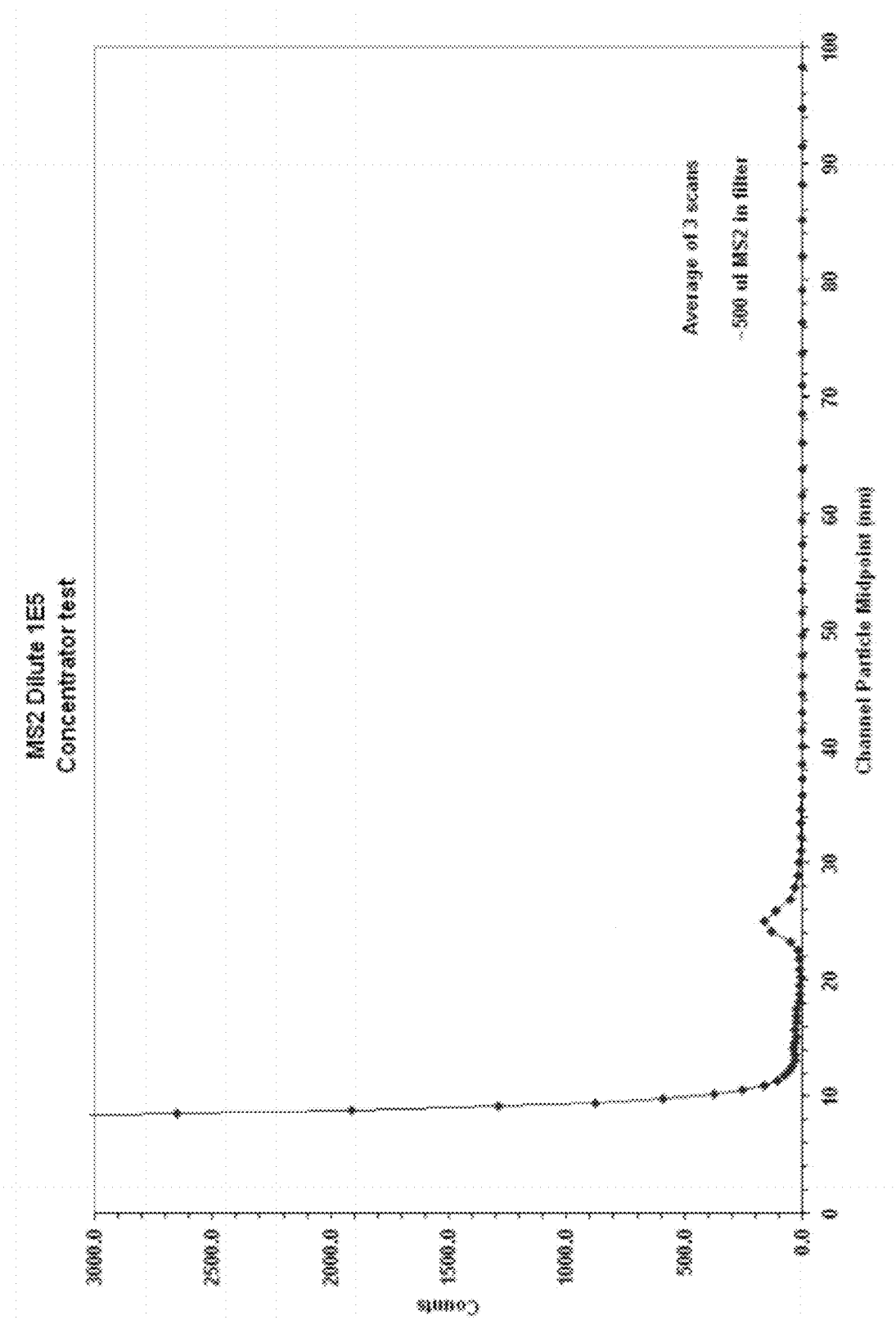
FIG. 4 is a graphical depiction of the GEMMA results for an initial MS2 bacteriophage sample.

FIG. 4 is a graphical depiction of the GEMMA results for an initial MS2 bacteriophage sample without concentration of the sample in the concentrator device 100 of FIGS. 2-3 (e.g., in the capillary inlet sample holder). A 500 μl sample of MS2 bacteriophage, initial sample concentration of approximately $1 \times 10^5$ particles/ml, was introduced (e.g., pipetted into) the sample holder and the sample was analyzed with the GEMMA device and the results of the count in the region of interest (ROI) are as shown in FIG. 4. An initial count in the ROI was 531, measured between 23.3 and 27.9 nm.

Example 2

Figure 5:
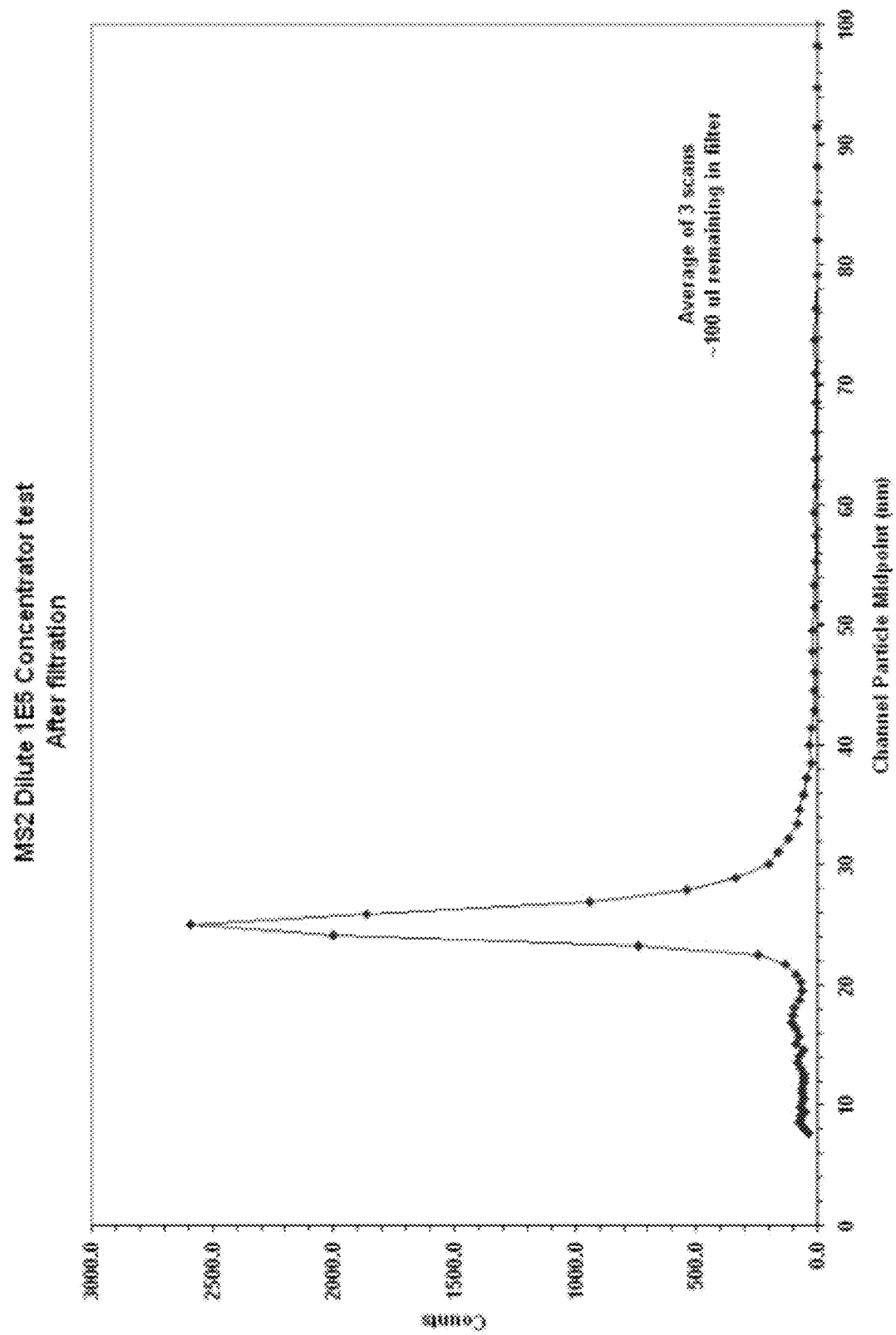
FIG. 5 is a graphical depiction of the GEMMA results for a MS2 bacteriophage sample after a four-minute concentration in the concentrator device shown in FIGS. 2-3.

FIG. 5 is a graphical depiction of the GEMMA results for a MS2 bacteriophage sample after a four-minute concentration in the concentrator device 100 shown in FIGS. 2-3. A 500 μl sample of MS2 bacteriophage, initial sample concentration of approximately $1 \times 10^5$ particles/ml, was introduced (e.g., pipetted into) a centrifugal ultrafiltration wedge filter such as, for example, a 100 KDa Ultrafree®-0.5 Centrifugal Filter Unit, available from Millipore Corp. of Billerica, Mass., USA. The filter was then inserted into the concentrator device (module) 100 and the sample was concentrated for four minutes to 100 μl and analyzed with the GEMMA device. The results of the count in the ROI are shown in FIG. 5. An initial count in the ROI was 8674, measured between 23.3 and 27.9 nm. Thus, the scans show a sixteen-fold increase in initial counts in ROI over the unconcentrated sample. In addition, concentration/filtration in the concentrator device 100 removed the large salt peak below 13 nm.

Example 3

Figure 6:
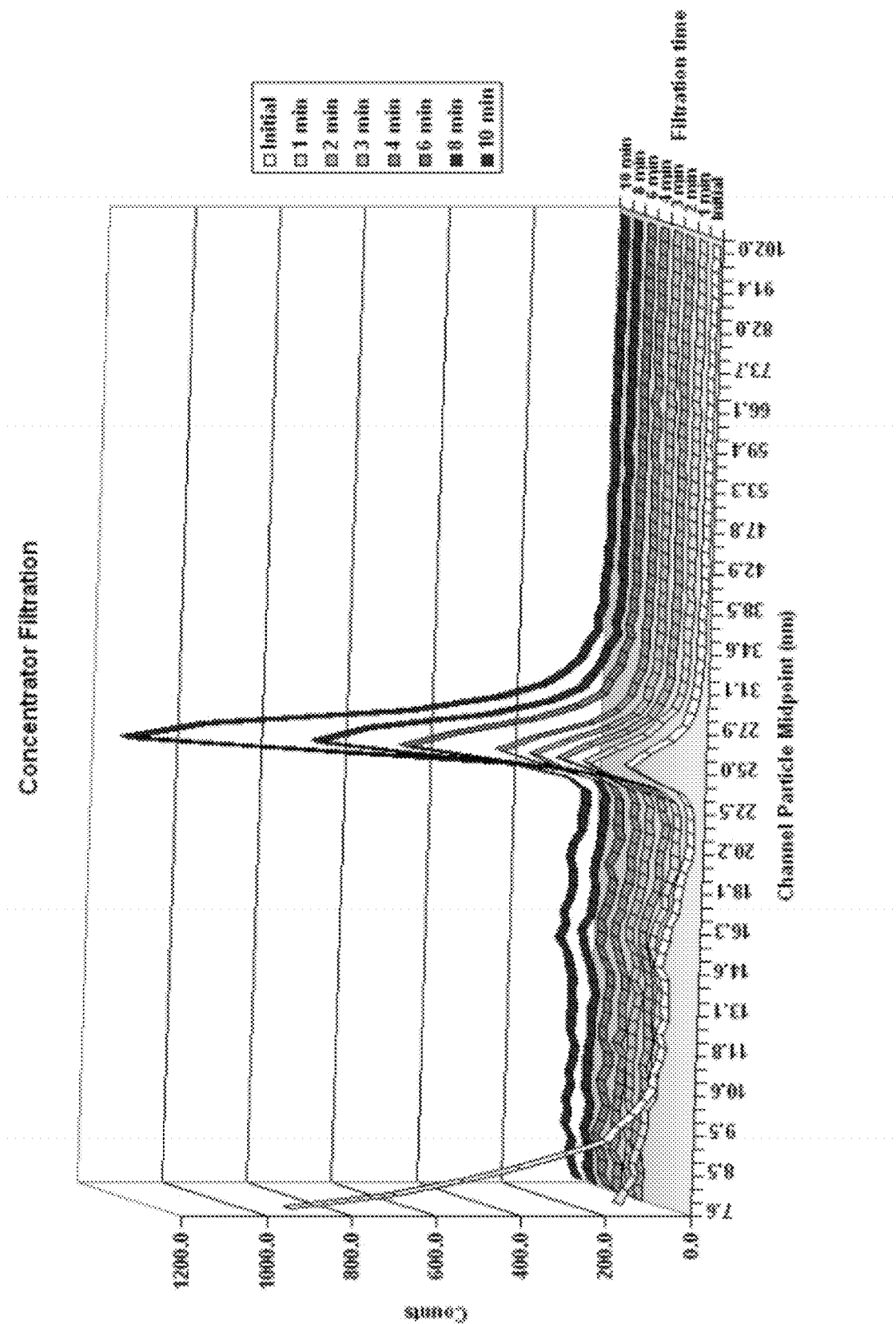
FIG. 6 is a graphical depiction of the GEMMA results for a MS2 bacteriophage sample based on measurements of partial concentrations taken in one-minute increments in the concentrator device shown in FIGS. 2-3.

FIG. 6 is a graphical depiction of the GEMMA results for a MS2 bacteriophage sample based on measurements of partial concentrations taken in one-minute increments in the concentrator device 100 shown in FIGS. 2-3. A 500 μl sample of MS2 bacteriophage, initial sample concentration of approximately $1 \times 10^5$ particles/ml, was introduced (e.g., pipetted into) a centrifugal ultrafiltration wedge filter such as, for example, a 100K Da Ultrafree®-0.5 Centrifugal Filter Unit, available from Millipore Corp. of Billerica, Mass., USA. The filter was then inserted into the concentrator device (module) 100. The sample was concentrated/filtered in one minute increments and analyzed at the end of each increment with the GEMMA device. The filtration was stopped when the sample reached a volume of approximately 80 μl at a time of 10 minutes. The results of the count at the end of each one minute increment in the ROI are shown in FIG. 6. The MS2 counts in the ROI (23.3-27.9 nm) increased with each increment of filtration and are listed in Table 1.

TABLE 1

MS2 Counts from Timed Concentrator Analyses

| Time (min) | ROI Counts (23.3-27.9 nm) |
|---|---|
| 0 | 559 |
| 1 | 812 |
| 2 | 883 |
| 3 | 1023 |
| 4 | 1153 |
| 6 | 1793 |
| 8 | 2432 |
| 10 | 3744 |

In addition, as can be seen in the graph in FIG. 6, concentration/filtration of the sample in the concentrator device 100 removed the large salt peak below 13 nm after the first minute of filtration and the subsequent scans were clean below 15 nm.

While an embodiment of the invention is described above, it should be understood that the foregoing is presented by way of example only, and not limitation. Thus, the breadth and scope of the invention should not be limited by the above-described embodiment, but should instead be defined only in accordance with the following claims and their equivalents.

What is claimed is:

1. A liquid sample concentrator device comprising:
 a pressure vessel including:
  an inlet configured to introduce pressurized air into a first portion of the pressure vessel;
  a first outlet fluidly coupled with a second portion of the pressure vessel and adapted to be selectively opened and closed; and
  a second outlet configured to receive a capillary tube inserted into the first portion of the pressure vessel; and
 a filter element disposed within the pressure vessel and configured to receive a liquid sample to be concentrated, wherein the filter element comprises a centrifugal ultra-filtration element having a predetermined molecular weight cut-off value, and wherein the filter element substantially separates the first portion of the pressure vessel from the second portion of the pressure vessel and defines a retentate side adjacent to the first portion and a filtrate side adjacent to the second portion, whereby when pressurized air is introduced through the inlet and the first outlet is open, a filtrate of the liquid sample received in the filter element passes from the retentate side to the filtrate side such that a concentrated retentate of the liquid sample remains on the retentate side, and whereby when the first outlet is closed, the concentrated retentate of the liquid sample is forced out through the capillary tube.

2. The liquid sample concentrator device according to claim 1, wherein the pressure vessel comprises:
 a hollow outer housing having an open end and including the inlet and the first and second outlets; and
 an inner member configured to be removeably received within the hollow outer housing through the open end and defining an interior cavity configured to receive the filter element, wherein when the inner member is received in the hollow outer housing, the interior cavity of the inner member is fluidly coupled with the first outlet.

3. The liquid sample concentrator device according to claim 2, wherein the inner member comprises an outer surface disposed adjacent to an inner surface of the hollow outer housing when received therein, and wherein a seal element is disposed between the outer surface of the inner member and the inner surface of the hollow outer housing to separate the first and second portions of the pressure vessel.

4. The liquid sample concentrator device according to claim 3, wherein the inner member and hollow outer housing comprise cylindrical elements and the seal element comprises at least one elastomeric O-ring seal.

5. The liquid sample concentrator device according to claim 2, further comprising a filtrate element configured to be received within the interior cavity of the inner member, wherein the filtrate element is configured to receive the filter element and includes an opening configured to be fluidly coupled to the first outlet.

6. The liquid sample concentrator device according to claim 1, further comprising an electrically conductive wire extending through the first portion of the pressure vessel and having an end configured to be positioned proximate the retentate side of the filter element.

7. The liquid sample concentrator device according to claim 1, where the first outlet comprises an adjustable valve.

8. The liquid sample concentrator device according to claim 1, wherein the inner member and the hollow outer housing are removeably coupled to one another by at least one of a friction fit, a snap fit, a bayonet connection, a fastener connection, a latch connection, and/or a threaded connection.

9. The device of claim 1, further comprising:
 a gas-phase electrophoretic mobility molecular analysis (GEMMA) device including an electrospray unit, wherein a capillary tube of the electrospray unit is received in the second outlet, and wherein an inlet end of the capillary tube is positioned proximate the retentate side of the filter element, for detecting the presence of submicron sized particles in a sample taken from the environment.

10. The apparatus according to claim 9, further comprising an electrically conductive wire extending through the first portion of the pressure vessel and having an end positioned proximate the retentate side of the filter element.

11. A method for concentrating a liquid sample, comprising:
 introducing a predetermined amount of a liquid sample to be concentrated into a filter element disposed within a pressure vessel;
 introducing pressurized air into a first portion of a pressure vessel on a retentate side of the filter element;
 opening a first outlet fluidly coupled with a second portion of the pressure vessel, whereby a filtrate of the liquid sample passes through the filter element to the second portion from the retentate side;
 closing the first outlet when a predetermined amount of the liquid sample remains on the retentate side of the filter or after a predetermined amount of time, whereby when the first outlet is closed, a concentrated retentate of the liquid sample is forced through an inlet end of a capillary tube positioned proximate the retentate side of the filter element and;
 introducing the concentrated retentate from the capillary tube to an electrospray unit of a gas-phase electrophoretic mobility molecular analysis (GEMMA) device to detect the presence of submicron-sized particles in the liquid sample.

\* \* \* \* \*